(12) United States Patent
Otsubo et al.

(10) Patent No.: US 8,864,734 B2
(45) Date of Patent: Oct. 21, 2014

(54) DISPOSABLE PANTS-TYPE WEARING ARTICLE

(75) Inventors: Toshifumi Otsubo, Kanonji (JP);
Tatsuya Hashimoto, Kanonji (JP);
Mariko Yamashita, Kanonji (JP)

(73) Assignee: Unicharm Corporation, Ehime (JP)

( * ) Notice: Subject to any disclaimer, the term of this patent is extended or adjusted under 35 U.S.C. 154(b) by 60 days.

(21) Appl. No.: 13/521,813

(22) PCT Filed: Jan. 21, 2011

(86) PCT No.: PCT/JP2011/051125
§ 371 (c)(1),
(2), (4) Date: Jul. 12, 2012

(87) PCT Pub. No.: WO2011/090171
PCT Pub. Date: Jul. 28, 2011

(65) Prior Publication Data
US 2012/0289922 A1    Nov. 15, 2012

(30) Foreign Application Priority Data
Jan. 21, 2010    (JP) ................... 2010-011404

(51) Int. Cl.
*A61F 13/15*    (2006.01)

(52) U.S. Cl.
USPC ............ 604/385.24; 604/385.25; 604/385.29; 604/385.3; 604/394; 604/396; 604/385.27

(58) Field of Classification Search
USPC ............... 604/385.24, 385.25, 385.29, 385.3, 604/394, 396, 385.27
See application file for complete search history.

(56) References Cited

U.S. PATENT DOCUMENTS

| 2004/0030317 | A1 | 2/2004 | Torigoshi |
| 2005/0010186 | A1 | 1/2005 | Otsubo et al. |
| 2008/0125741 | A1* | 5/2008 | Tsuji et al. ............... 604/385.29 |
| 2009/0275911 | A1* | 11/2009 | Hormung et al. ........ 604/385.28 |

FOREIGN PATENT DOCUMENTS

| EP | 0547497 | A2 | 6/1993 |
| EP | 0743052 | A2 | 11/1996 |
| EP | 2221034 | A1 | 8/2010 |
| JP | 62243806 | A | 10/1987 |
| JP | 5247701 | A | 9/1993 |

(Continued)

OTHER PUBLICATIONS

International Search Report and Written Opinion for PCT/JP2011/051125, dated May 10, 2011.

*Primary Examiner* — Jacqueline F. Stephens
(74) *Attorney, Agent, or Firm* — Lowe Hauptman & Ham LLP

(57) ABSTRACT

The present invention provides a disposable pants-type wearing article free from possibility that upper regions of the leg-openings' peripheral edges might be formed with frills even when the belt-like leg elastic members contract along the peripheral edges of the respective leg-openings. Belt-like leg elastic members in a disposable pants-type diaper each has inner and outer surfaces at least one of which is bonded to sheet-like members included in put flat and joined together regions and a crotch region of the diaper. The belt-like leg elastic members extend from the respective put flat and joined regions along leg-openings' peripheral edges. Over ranges in which the belt-like leg elastic members extend along the respective peripheral edges the sheet-like members also extend along the peripheral edges.

7 Claims, 8 Drawing Sheets

(56) References Cited

FOREIGN PATENT DOCUMENTS

| | | | |
|---|---|---|---|
| JP | 7308341 A | 11/1995 | |
| JP | 2002159529 A | 6/2002 | |
| JP | 2003230595 A | 8/2003 | |
| JP | 2003290284 A | 10/2003 | |
| JP | 3488506 B2 | 1/2004 | |
| JP | 2008173285 A | 7/2008 | |
| JP | 2009136583 A | 6/2009 | |
| JP | 2010233733 A | 10/2010 | |
| JP | 2010233945 A | 10/2010 | |
| WO | 2009072326 A1 | 6/2009 | |
| WO | 2010113472 A1 | 10/2010 | |
| WO | 2010113510 A1 | 10/2010 | |

\* cited by examiner

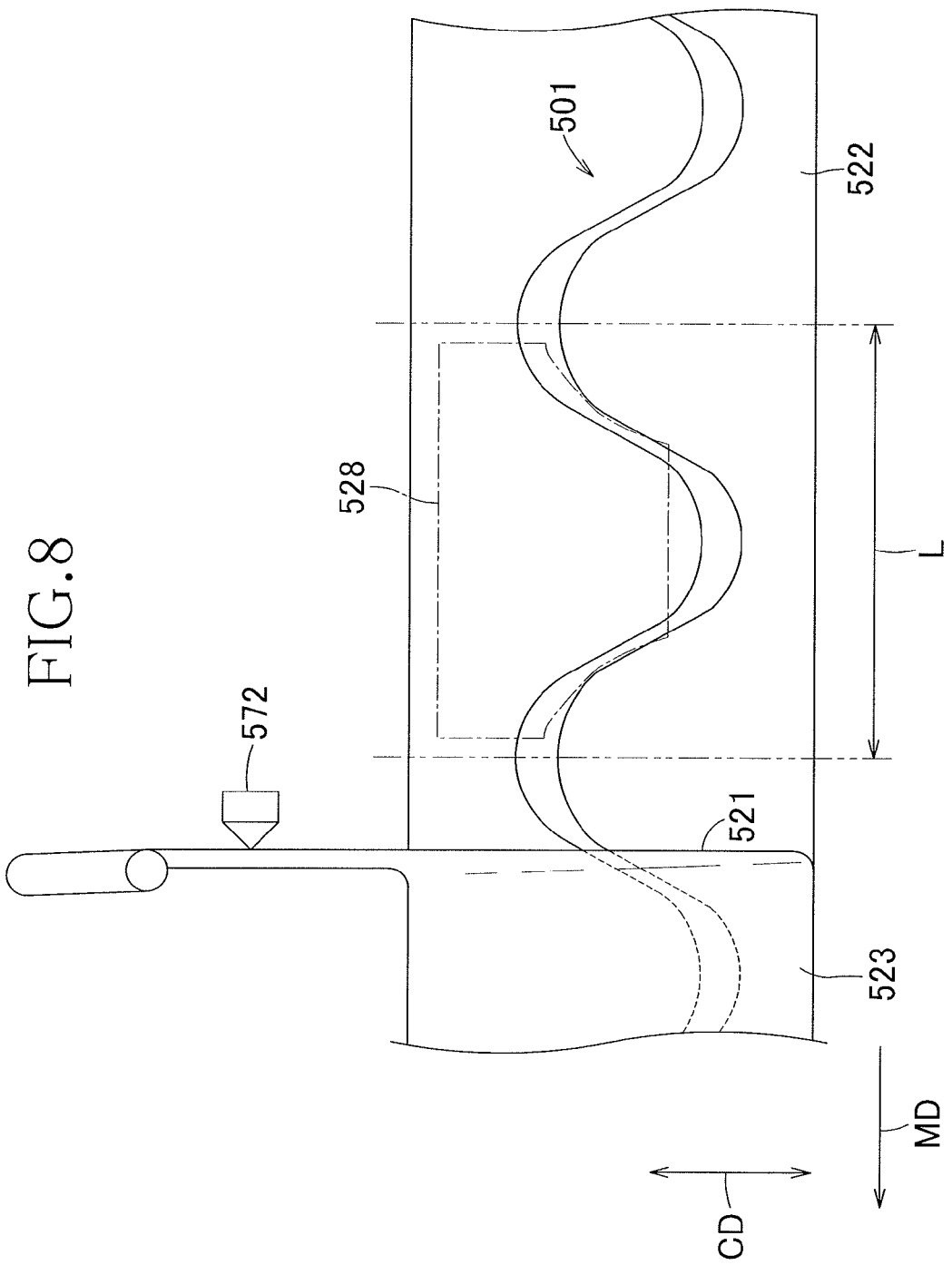

DISPOSABLE PANTS-TYPE WEARING ARTICLE

RELATED APPLICATIONS

The present application is a National Phase of International Application Number PCT/JP2011/051125, filed Jan. 21, 2011, and claims priority from Japanese Application Number 2010-011404, filed Jan. 21, 2010.

TECHNICAL FIELD

The present invention relates to disposable pants-type wearing articles suitable for use as disposable diapers or the like.

BACKGROUND

Conventionally, disposable pants-type diapers which are formed by putting respective opposite side edges of front and rear waist regions flat together and bonding them together are known.

For example, in disposable absorbent pants disclosed in JP S62-243806 A (PTL 1), front and rear waist regions are put flat and joined together by a sealing treatment under pressure along respective opposite side edges of these front and rear waist regions. Belt-like leg elastic members extending in a transverse direction or belt-like leg elastic members extending in a longitudinal direction are bonded to the front and rear waist regions, respectively. These leg elastic members are formed, for example, of urethane foam or the like and have relatively large width dimension of about 10 to about 45 mm.

In a disposable diaper disclosed in JP 3488506 B2 (PTL 2), belt-like leg elastic sheet members are attached under even tension in a longitudinal direction thereof to a base material sheet forming the diaper. On the base material sheet cut in generally hourglass-shape, the leg elastic sheet members respectively draw concave curved lines in a crotch region.

In a pants-type absorbent article disclosed in JP 2008-173285 A (PTL 3), a front waist region and a rear waist region are and joined together along side seams by a sealing treatment such as a heat-sealing or ultrasonic sealing treatment. Two or more straight belt-like leg-gather strips are attached to peripheral edges of respective leg-openings in a manner that these leg-gather strips may be obliquely crossed so as to draw curved lines along the peripheral edges of the respective leg-openings. One of the leg-gather belt-like strips extends horizontally and is spaced from the peripheral edges of the respective leg-openings.

CITATION LIST

Patent Literature

{PTL 1} JP S62-243806 A
{PTL 2} JP 3488506 B2
{PTL 3} JP 2008-173285 A

SUMMARY

Technical Problem

Among various embodiments of disposable pants-type wearing articles inclusive of the disposable pants-type diapers, the articles arranged to be formed along peripheral edges of the respective leg-openings with frills are known. However, according to the inventors' findings, there is a noticeable trend that not a few consumers rather desire to use the pants-type wearing articles designed to be not formed with frills. Despite such trend, among the disposable pants-type wearing articles using belt-like leg elastic members each having a width dimension as wide as, for example, 5 mm or more, there are no wearing articles satisfying such consumers' trend as far as the inventors know. In the wearing articles disclosed in PTL 1 and PTL 3, the segments of the belt-like leg elastic members horizontally extending along upper segments of the leg-openings' peripheral edges are spaced from the peripheral edges of the respective leg-openings. With such arrangement, frills are formed between the leg elastic members and the peripheral edges of the associated leg-openings. In the wearing article disclosed in PTL 2, no frills are formed along the peripheral edges of the leg-openings but the segments of the belt-like leg elastic sheets forming the curved lines as a whole rectilinearly extend in the longitudinal direction of the wearing article. Specifically, the segments of the belt-like leg elastic sheets lying along the upper regions of the respective leg-openings do not contract along the peripheral edges of the respective leg-openings.

An object of the present invention is to provide a disposable pants-type wearing article free from possibility that upper regions of the leg-openings' peripheral edges might be formed with frills even when the belt-like leg elastic members contract along the peripheral edges of the respective leg-openings.

Solution to Problem

According to the present invention, there is provided a disposable pants-type wearing article having a front-back direction, a vertical direction and a transverse direction being orthogonal to one another and including:

a front waist region and a rear waist region opposed to each other in the front-back direction, and a crotch region extending between these two waist regions;

put flat and joined together regions formed of putting flat and joining together the front and rear waist regions along respective side edges of the front and rear waist regions respectively opposed in the transverse direction and extending in the vertical direction;

a waist-opening and a pair of leg-openings formed of cooperation of the front and rear waist regions with the crotch region; and belt-like leg elastic members extending under tension along respective peripheral edges of the leg-openings, wherein the belt-like leg elastic members respectively have inner sides facing skin of the wearer of the wearing article and outer surfaces opposite to the inner side at least one of which is bonded to a sheet-like member included in the put flat and joined together regions and the crotch region.

The belt-like leg elastic members respectively extend, on a font side and a rear side of the wearing article, from the put flat and joined together regions, along peripheral edges of the leg elastic members and the sheet-like member also extends along the peripheral edges over ranges in which the belt-like leg elastic members extend along the peripheral edges.

According to one embodiment of the present invention, a dimension of the range in which the belt-like leg elastic members extend as measured in the vertical direction is at least 30% of a dimension of the let-openings as measured in the vertical direction so long as the wearing article is kept flat under tension in the vertical direction as well as in the transverse direction.

According to another embodiment of the present invention, the peripheral edges draw curved lines at least along parts thereof, respectively, and the belt-like leg elastic members are in a curved state along the parts so long as the wearing article is kept flat under tension in the vertical direction as well as in the transverse direction.

According to still another embodiment of the present invention, the crotch region is not formed over the range in which the belt-like leg elastic members extend with frills even when the belt-like leg elastic members contract.

As used herein, the term "belt-like leg elastic members" means the elastic members each having the dimension in the transverse direction at least about 1.5 times the dimension in the thickness direction.

As used herein, the description "the sheet-like member is formed with frills" means that, upon contraction of the belt-like leg elastic members attached under tension to the sheet-like member, the edge of the sheet-like member spaced from the belt-like leg elastic members and extending in parallel to these belt-like leg elastic members is deformed so as to be undulated. The undulation is repeated in the direction in which the belt-like leg elastic members contract.

Advantageous Effects of Invention

In the disposable pants-type wearing article according to the present invention, the belt-like leg elastic members extend from the put flat and joined together regions which are formed of the respective opposite side edges of the front and rear waist regions along the peripheral edges of the respective leg-openings. Over ranges in which the belt-like leg elastic members extend in this manner, the belt-like leg elastic members and the sheet-like members bonded thereto define respective parts of the leg-openings' peripheral edges. In consequence, over such ranges, the sheet-like members are not formed with frills even when the belt-like leg elastic members contract.

BRIEF DESCRIPTION OF DRAWINGS

FIG. 8 is a view similar to FIG. 6, exemplarily showing the state in which an elastic web is bonded to the nonwoven fabric web.

DESCRIPTION OF EMBODIMENTS

Details of a disposable pants-type wearing article according to the present invention will be more fully understood from the description given hereunder with reference to the accompanying drawings.

Figure 1:
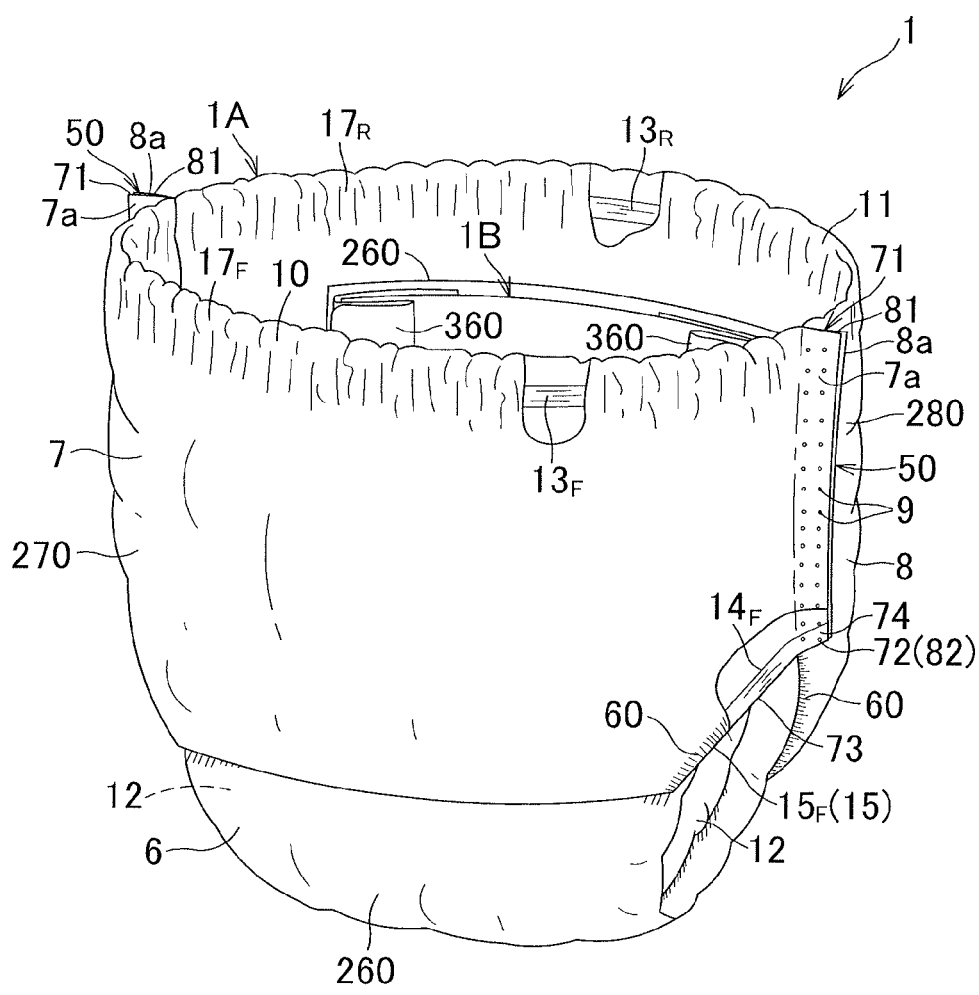
FIG. 1 is a partially cutaway perspective view of a disposable pants-type wearing article (pants-type diaper).
Figure 2:
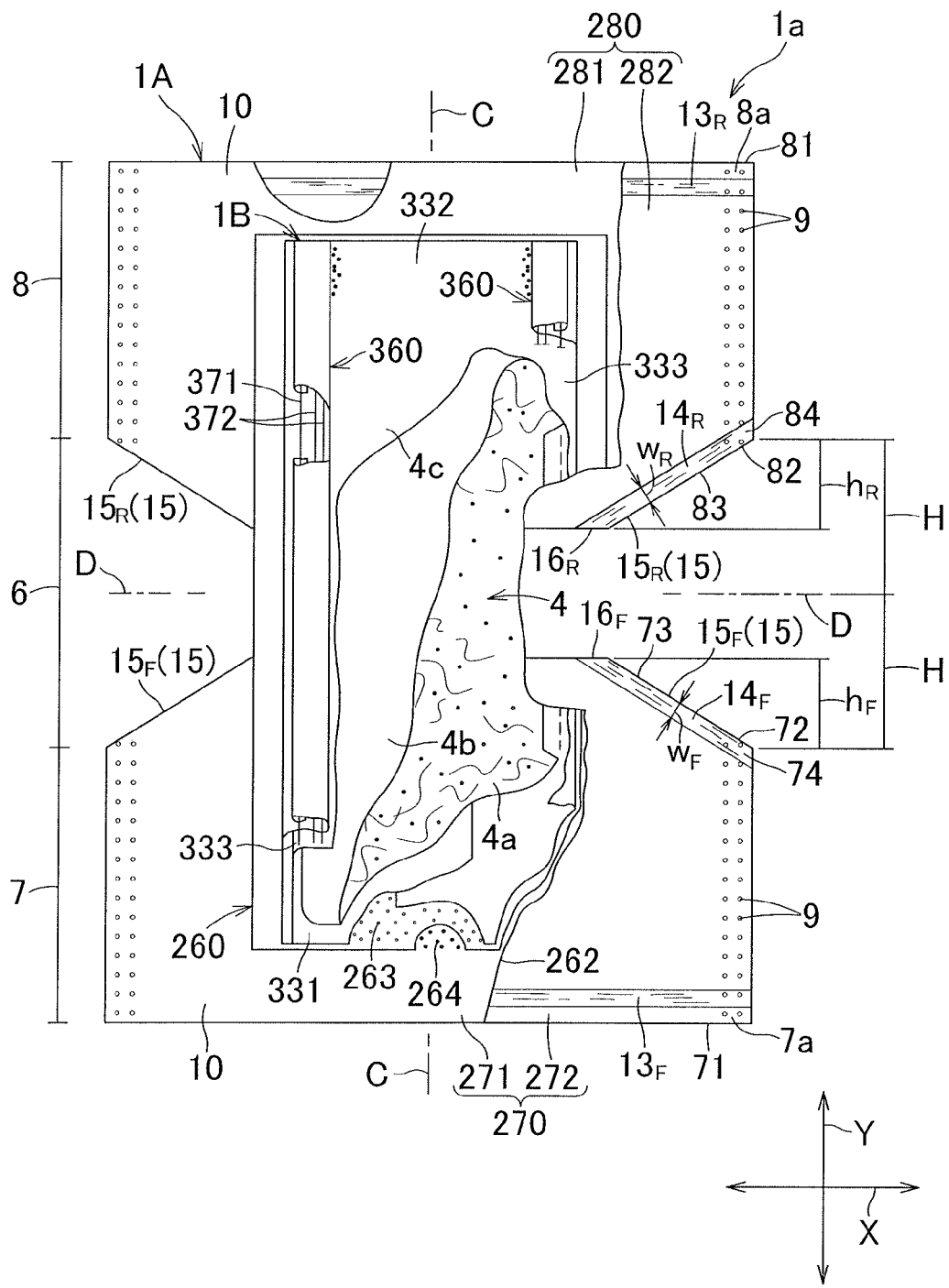
FIG. 2 is a partially cutaway plan view of the flatly developed diaper.

FIG. 1 a partially cutaway perspective view of a pants-type diaper 1 as one example of disposable pants-type wearing articles according to the present invention wherein a transverse direction, a front-back direction and a vertical direction are designated by double-headed arrows X, Y and Z, respectively. The diaper 1 includes a pants-shaped chassis 1A and a bodily fluid-absorbent structure 1B attached to an inner surface of the chassis 1A. The chassis 1A includes a crotch region 6, a front waist region 7 extending forward with respect to the crotch region 6 and a rear waist region 8 extending rearward with respect to the crotch region 6. The front and rear waist regions 7, 8 are put flat and joined together along respective opposite edges 7a, 7a; 8a, 8a thereof by sealing spots 9 arranged intermittently in the vertical direction Z to form put flat and joined together regions 50. In the diaper 1, the front and rear waist regions 7, 8 cooperate with the crotch region 6 to form a waist-opening 11 and a pair of leg-openings 12. The chassis 1A further includes a front sheet assembly 270 extending over a whole area of the front waist region 7 and additionally over an upper half of the crotch region 6 on its front side and a rear sheet assembly 280 extending over a whole area of the rear waist region 8 and additionally over an upper half of the crotch region 6 on its rear side (See FIGS. 2 and 3). The front sheet assembly 270 is provided with a belt-like front waist-elastic member $13_F$ extending along a peripheral edge 10 of the waist-opening 11 and belt-like front side leg elastic members $14_F$ extending along front halves $15_F$ of the peripheral edges 15 of the respective leg-openings 12 are attached under tension to the front sheet assembly 270. The rear sheet assembly 280 is provided with a belt-like rear waist-elastic member $13_R$ extending along a peripheral edge 10 of the waist-opening 11 and belt-like rear side leg elastic members $14_R$ extending along rear side peripheral edges $15_R$ of the respective leg-openings 12 as shown in FIG. 2 are attached under tension to the front sheet assembly 270. It should be appreciated that these elastic or elastic members, $13_F$, $13_R$, $14_F$ and $14_R$ are in contracted state in the diaper 1 shown in FIG. 1.

Figure 3:
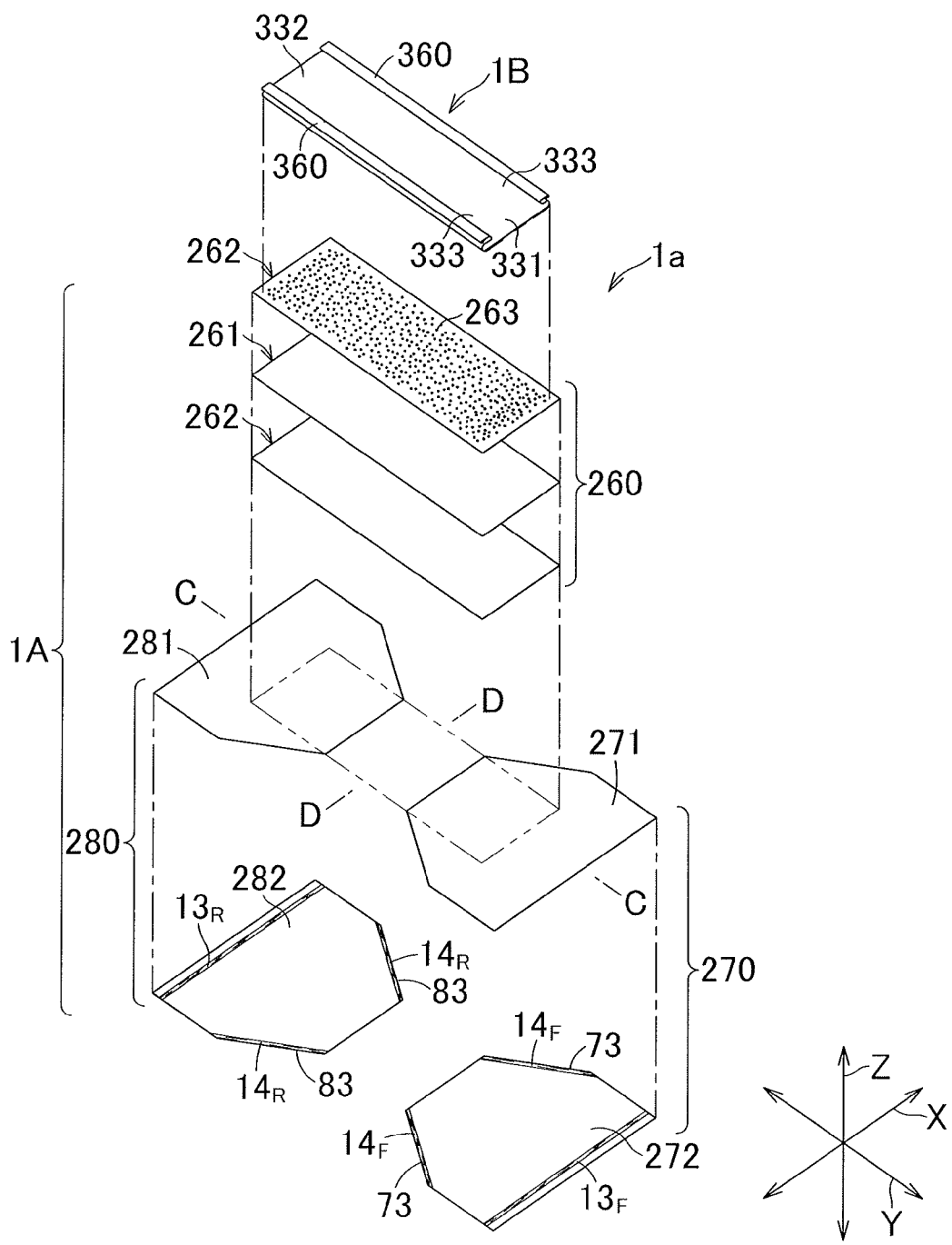
FIG. 3 is an exploded perspective view of the flatly developed diaper.

FIG. 2 is a partially cutaway plan view of the diaper 1a having the front and rear waist regions 7, 8 peeled off each other along the put flat and joined together regions 50 and flatly developed in the transverse direction X and the front-back direction Y and FIG. 3 is an exploded perspective view of the flatly developed diaper 1a. The respective regions extending in the vertical direction Z in FIG. 1 extend in the front-back direction Y in FIGS. 2 and 3. In FIG. 2, a front-back center line C-C and a transverse center line D-D extending orthogonally to the front-back center line C-C to bisect a dimension of the developed diaper 1a in the front-back direction Y are indicated. The developed diaper 1a is shaped symmetrically about the front-back center line C-C.

In referring to FIGS. 2 and 3, the chassis 1A includes a substantially hexagonal front sheet assembly 270 defining the front waist region 7, a substantially hexagonal rear sheet assembly 280 defining the rear waist region 8 and a part of the crotch region 6 and a rectangular central sheet assembly 260 defining a part of the crotch region 6. In the front sheet assembly 270, the front side peripheral edges $15_F$ rectilinearly extend so as to intersect obliquely with the center line C-C and, in the rear sheet assembly 280, the rear side peripheral edges $15_R$ rectilinearly extend so as to intersect obliquely with the center line C-C.

The front sheet assembly 270 includes an inner sheet 271 and an outer sheet 272 which are same in shape as well as in size. Between these sheets 271, 272, the single belt-like front waist-elastic member $13_F$ and a pair of front side leg-elastic members $14_F$ are sandwiched and attached under tension to at least one of these inner sheet 271 and outer sheet 272 with hot melt adhesives (not shown). The belt-like front side leg elastic members $14_F$ respectively have lower edges 73 falling into lines with the respective front side peripheral edges $15_F$ defined by the inner sheet 271 and the outer sheet 272. In other words, the front side peripheral edges $15_F$ are defined by these sheets 271, 272 and the belt-like front side leg elastic members $14_F$. Respective inner surfaces of the elastic members $13_F$, $14_F$ facing the wearer's skin (not shown) are covered with the inner sheet 271.

The rear sheet assembly 280 includes an inner sheet 281 and an outer sheet 282 which are the same in shape as well as in size. Between these sheets 281, 282, the single belt-like rear waist-elastic member $13_R$ and a pair of front side leg-elastic members $14_R$ are sandwiched and attached under tension to at least one of these inner sheet 281 and outer sheet 282 with hot melt adhesives (not shown). The belt-like rear side leg elastic members $14_R$ respectively have lower edges 83 falling into lines with the respective rear side peripheral edges $15_R$ defined by the inner sheet 281 and the outer sheet 282. In other words, the rear side peripheral edges $15_R$ are defined by these sheets 281, 282 and the belt-like rear side leg elastic members $14_R$. The respective inner surfaces of the elastic members $13_R$, $14_R$ facing the wearer's skin (not shown) is covered with the inner sheet 281.

The central sheet 260 includes a rectangular leakage-barrier film 261 sandwiched between a pair of cover sheets 262 wherein these film and sheets are bonded to one another with hot melt adhesives (not shown). The leakage-barrier film 261 is formed of a liquid-impervious plastic film and the cover sheet 262 is formed of a fibrous nonwoven fabric. Front and rear ends of the central sheet assembly 260 respectively extend onto respective inner surfaces (i.e., upper surfaces as viewed in FIG. 3) of the front sheet assembly 270 and the rear sheet assembly 280 and are respectively bonded to these inner surfaces with hot melt adhesives 264 (See FIG. 2) so as to connect the front sheet assembly 270 with the rear sheet assembly 280. The bodily fluid-absorbent structure 1B is bonded to the inner surface of the central sheet assembly 260 with hot melt adhesives 263 applied to the inner surface of the central sheet assembly 260.

The bodily fluid-absorbent structure 1B includes, as shown in FIG. 2, has a rectangular shape which is relatively long in the front-back direction and this shape is contoured by a pair of opposite side edges 333 extending in parallel to the center line C-C and front and rear ends 331, 332 extending in parallel to the center line D-D. The respective side edges 333 are formed with leakage-barriers 360 known in the name of the three dimensional gather in the art. In such bodily fluid-absorbent structure 1B, a liquid-previous absorbent material 4a such as fluff pulp and super-absorbent polymer particles is covered with a wrapping sheet 4b formed of liquid-previous tissue papers or fibrous nonwoven fabrics and the side of this wrapping sheet 4b facing the wearer's skin is covered with a liquid-previous skin-contact sheet 4c. The leakage-barriers 360 are preferably formed of a liquid-impervious sheet. High leakage-barrier effect of the bodily fluid-absorbent structure 1B is assured by the leakage-barriers 360 and indirect back up of the liquid-impervious inner sheet 261 constituting the central sheet assembly 260.

Rubber threads 371, 372 extending in the front-back direction Y as viewed in FIG. 2 are bonded under tension to the liquid-impervious sheet forming the leakage-barriers 360 of the bodily fluid-absorbent structure 1B with hot melt adhesives (not shown). While the liquid-impervious sheet is folded in a Z-shape or in an inverted Z-shape in the developed diaper 1a of FIG. 2, the leakage-barriers 360 raise themselves on the inner surface of the skin-contact sheet 4c along the side edges 333 of the bodily fluid-absorbent structure 1B under contraction of the rubber threads 371, 372.

In the developed diaper 1a as has been described above with reference to FIG. 2, the inner sheets 271, 281 and the outer sheets 272, 282 may be formed of sheet-like members such as fibrous nonwoven fabrics containing thermoplastic synthetic fibers, plastic films formed of thermoplastic synthetic resins or a laminated of these nonwoven fabrics and plastic films. More preferably, these inner and outer sheets 271, 281; 272, 282 may be formed of spun bonded nonwoven fabrics, melt blown nonwoven fabrics or a laminate SMS nonwoven fabrics of spun bonded nonwoven fabrics, melt blown nonwoven fabrics and spun bonded nonwoven fabrics. In every case, a mass per unit area thereof is ranging from about 10 to about 100 g/m². The front side belt-like leg elastic members $14_F$ and the rear side belt-like leg elastic members $14_R$ may be formed of the belt-like sheets containing at least one of the natural rubbers and the synthetic rubber as rubber ingredients. These belt-like leg elastic members $14_F$, $14_R$ may be preferably formed of elastically stretchable nonwoven fabrics made of elastic yarns or threads containing urethane rubbers or the like as rubber ingredients or plastic films having a mass per unit area ranging from about 20 to about 100 g/m². More preferably, these belt-like leg elastic members $14_F$, $14_R$ may be formed of the elasticized fibrous nonwoven fabric made of elastic yarns or threads containing the rubber ingredients such as urethane rubbers or the elasticized nonwoven fabrics of elastic yarns or threads and inelastic thermoplastic synthetic fibers wherein the elastic yarns or threads of at least about 30% by mass are contained therein. Referring to FIG. 2, both a width dimension $W_F$ of the front side leg elastic member $14_F$ and a width dimension $W_R$ of the rear side leg elastic member $14_R$ are the dimensions measured in the direction which is orthogonal to the direction in which these elastic members extend. These width dimensions $W_F$ and $W_R$ are preferably at least about 5 mm and more preferably ranges about 7 to about 40 mm. Thickness dimension of these elastic members $14_F$, $14_R$ preferably ranges about 0.2 to about 1.5 mm. Thickness dimensions of the nonwoven fabrics, the plastic films, the belt-like waist-elastic members $13_F$, $13_R$ and the belt-like leg elastic members $14_F$, $14_R$ as have been indicated were values measured using Automatic Compression Tester "KES-FB3-AUTO-A" (manufactured by KATO TECH CO., LTD. in Japan) when compression force of about 0.5 g/cm² was exerted on the respective test pieces.

While the front waist-elastic member $13_F$ and the rear waist-elastic member $13_R$ in the developed diaper 1a are preferably belt-like elastic members each having a width dimension of about 10 to about 40 mm, it is also possible to use a plurality of rubber threads each having a diameter or a width dimension of about 0.3 to about 3 mm as the front waist-elastic member $13_F$ and the rear waist-elastic member $13_R$. In the developed diaper 1a, the front waist-elastic member $13_F$ and the front side leg elastic members $14_F$ are in a state appropriately stretched in the longitudinal direction, for example, at a ratio of about 1.5 to about 4.0 and the rear waist-elastic member $13_R$ and the rear side leg members $14_R$ are also in a state appropriately stretched in the longitudinal direction, for example, at a ratio of about 1.5 to about 4.0.

The developed diaper 1a of FIG. 2 is folded back along the center line D-D with the bodily fluid-absorbent structure 1B inside and thereby the respective side edges 7a, 7a; 8a, 8a of the front and rear waist regions 7, 8 are put flat together. The side edges 7a, 7a; 8a, 8a put flat together in this manner may be set between horns and anvils of an ultrasonic sealer and ultrasonic treated to form a plurality of sealing spots 9 in which the respective side edges 7a, 7a; 8a, 8a of the front and rear waist regions 7, 8 are joined and these sealing spots 9 form the respective put flat and joined together regions 50. Now the developed diaper 1a is converted to the flat diaper 1 under tension in the transverse direction X as well as in the longitudinal direction Y. In the developed diaper 1a, a dimension of the side edge 7a in the front-back direction Y is the same as that of the side edge 8a in the front-back direction Y and upper and lower edges 71, 72 of the side edge 7a in the put flat and joined together regions 50 (See FIG. 1) of the diaper 1 come into line with upper and lower ends 81, 82 of the side edge 8a, respectively.

A reference sign H in the developed diaper 1a of FIG. 2 indicates a distance from the center line D-D to the lower edge 72 of the side edge 7a and a distance from the center line D-D to the lower edge 82 of the side edge 8a. This dimension H is a value measured in parallel to the center line C-C and this dimension is the same as a dimension of the leg-opening 12 in the vertical direction Z so long as the diaper 1 is kept in the state of tension in the transverse direction X and in the vertical direction Z. A dimension $h_R$ indicates a distance from the lower edge 72 to the lower end $16_F$ of the front side leg elastic member $14_F$ and a dimension $h_R$ indicates a distance from the lower edge 82 to the lower end $16_R$ of the rear side leg elastic member $14_R$. These dimensions $h_F$, $h_R$ also are values measured in parallel to the center line C-C. As used herein, the terms "lower edge 72" and "lower edge 82" means the positions of the sealing spot 9 formed in the lowermost portion of the put flat and joined together region 50 in the diaper 1 (See FIG. 1). In the developed diaper 1a, in other words, in the diaper 1 kept in the state of tension in the transverse direction X as well as in the vertical direction Z, the values of the dimensions $h_F$, $h_R$ are preferably set to at least about 30% of the value of the dimension H so that the ranges of the leg-openings' entire peripheral edges as wide as possible may be put in close contact about the wearer's thighs at a high fit. While the dimension $h_F$ and the dimension $h_R$ are illustrated in FIG. 2 to be substantially equal to each other, the distance from the center line D-D to the lower end $16_F$ and the distance from the center line ID-D to the lower end $16_R$ may be differentiated to implement the present invention so that the dimension $h_F$ and the dimension $h_R$ may be different from each other.

Referring to FIGS. 1 and 2, the front side leg elastic members $14_F$ and the rear side leg elastic members $14_R$ extend along relatively upper segments of the peripheral edges of the respective leg-openings 12 so that the direction in which these elastic members contract substantially corresponds to the circumferential direction about the wearer's thighs. The front side leg elastic members $14_F$ cooperate with the front sheet assembly 270 to define the front side peripheral edges $15_F$ and the rear side leg elastic members $14_R$ cooperate with the rear sheet assembly 280 to define the rear side peripheral edges $15_R$. Upon contraction of these elastic members $14_F$, $14_R$, the front sheet assembly 270 and the rear sheet assembly 280 are formed in the vicinity of the front side peripheral edges $15_F$ and the rear side peripheral edges $15_R$ with fine wrinkles 60 (See FIG. 1) but not with the frills. In consequence, the diaper 1 can be put on the wearer's body as the diaper without being formed with the frills along the upper segments of the leg-openings' peripheral edges, more specifically, over ranges defined by upper about 30% or more of the height H of the respective leg-openings 12.

Referring again to FIGS. 1 and 2, the front side leg elastic members $14_F$ have front side upper ends 74 lying on the side edges 7a of the front waist region 7 and included in the put flat and joined together regions 50 and the rear side leg elastic members $14_R$ have rear side upper ends 84 lying on the side edges 8a of the rear waist region 8 and included in the put flat and joined together regions 50. In the put flat and joined together regions 50, the side edges 7a, 8a are subjected to pressurized sealing treatments such as ultrasonic sealing treatments to fusion-bond thermoplastic synthetic resins contained in these side edges 7a, 8a. In this way, the front side upper ends 74 and/or the inner sheet 271 covering this front side upper ends 74 are fusion-bonded to the rear side upper ends 84 and/or the inner sheet 281 covering this rear side upper ends 84 and thereby the sealing spots 9 are formed. Planar shape of the individual sealing spot 9 depends on a shape of the horns used in the ultrasonic treatment. However, if any ingredients having a rubber elasticity such as natural rubbers or synthetic rubbers contained in the front side leg elastic members $14_F$ and the rear side leg elastic members $14_R$ is present in the overlapping regions of the front side leg elastic members $14_F$ and the rear side leg elastic members $14_R$, it will be difficult to assure the side edges 7a, 8a to be joined together without an anxiety that these side edges might be readily peeled off one from another. To overcome such problem, the area ratio of the sealing spots per unit area in the overlapping region is preferably adjusted to be noticeably higher than that in the remaining regions so that the side edges 7a and the side edges 8a may be joined together without any possibility that these side edges might be readily peeled off one another.

Figure 4:
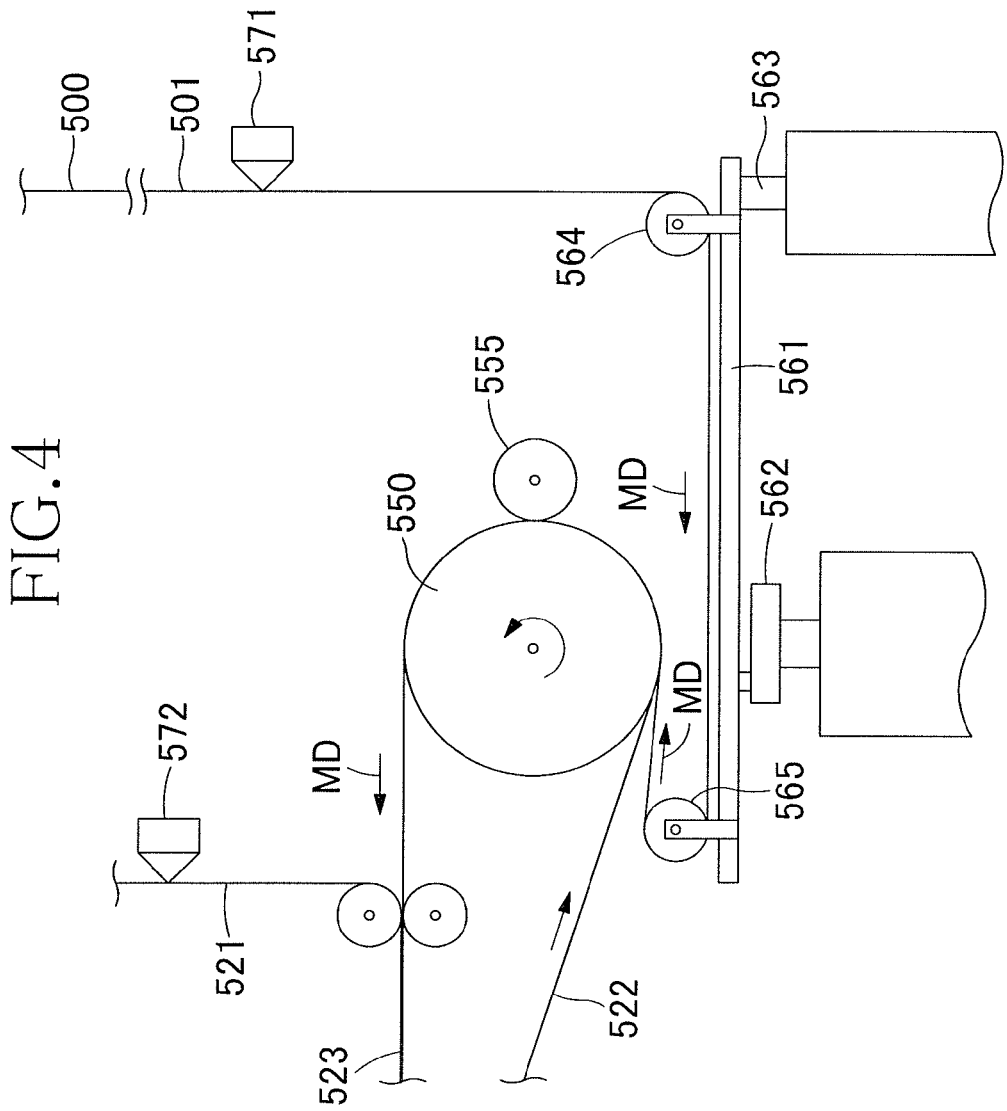
FIG. 4 is a schematic side view of main equipment used in a process for making a composite web.
Figure 5:
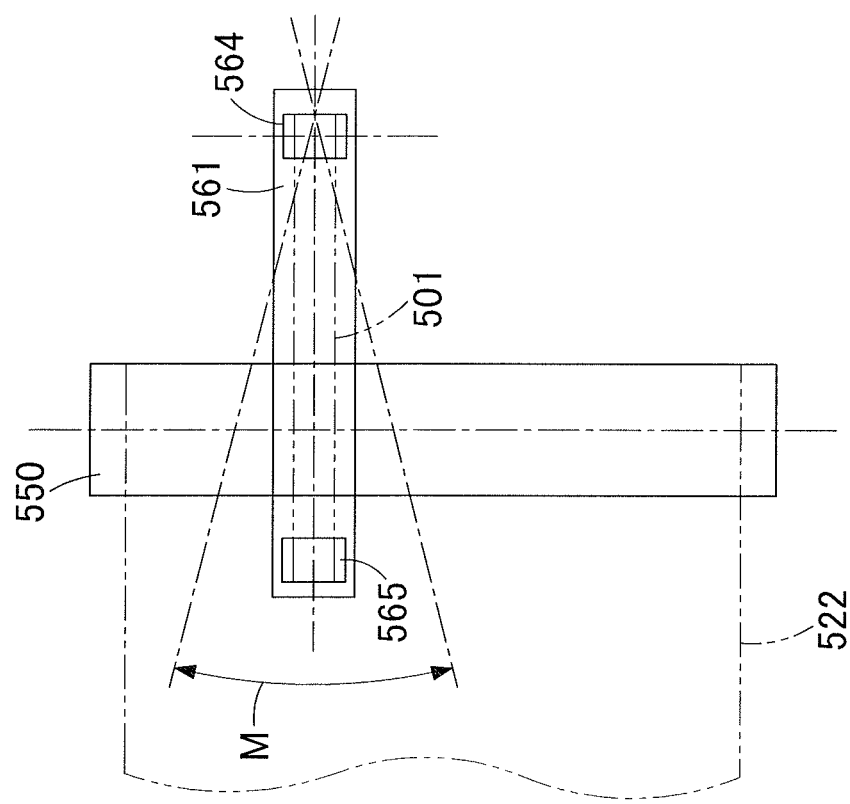
FIG. 5 is a schematic overhead view illustrating part of FIG. 4.

FIG. 4 is a schematic side view of main equipment used in a process for making the front sheet assembly 270 and the rear sheet assembly 280 exemplarily shown in FIGS. 2 and 3 and FIG. 5 is a schematic overhead view illustrating part of the main equipment. The process for making the sheet assembly is basically common to the front sheet assembly 270 and the rear sheet assembly 280 and, in view of this, description of the process will be made hereunder with respect to the front sheet assembly 270. Referring to FIG. 4, an elastic web 501 as a material web for the front side leg elastic member $14_F$ is continuously fed from above as viewed in FIG. 4 and coated by a first coater 571 with hot melt adhesives (not shown). The elastic web 501 corresponds to a raw fabric 500 having stretch properties and having been elastically stretched at a desired ratio. The elastic web 501 is guided by guide rolls 564, 565 mounted on a rocking arm 561 and fed in a machine direction MD indicated by an arrow to a joining roll 550 on which the elastic web 501 comes in contact with and bonded under a pressure to second nonwoven fabric web 522 continuously fed from the left-hand as viewed in FIG. 4. The second nonwoven fabric web 522 further runs in the direction indicated by an arrow and converges with a first nonwoven fabric web 521 which is, in turn, fed from above as viewed in FIG. 4 and coated by a second coater 572 with hot melt adhesives (not shown). In this way, the second nonwoven fabric web 522 is bonded to the first nonwoven fabric web 521 to form a composite web 523 sandwiching the elastic web 501 between these first nonwoven fabric web 521 and the second nonwoven fabric web 522. The first nonwoven fabric web 521 in the composite web 523 is used as one of the inner sheet 271 and the outer sheet 272 and the second nonwoven fabric web 522 in the composite web 523 is used as the other of the inner sheet 271 and the outer sheet 272. The rocking arm 561 is rocked to and from around a pivot shaft 563 by a driving unit 562 in a predetermined range of movement indicated by a double-headed arrow M in FIG. 5. In FIG. 5, the elastic web 501 and the second nonwoven fabric web 522 are indicated by imaginary lines.

Figure 6:
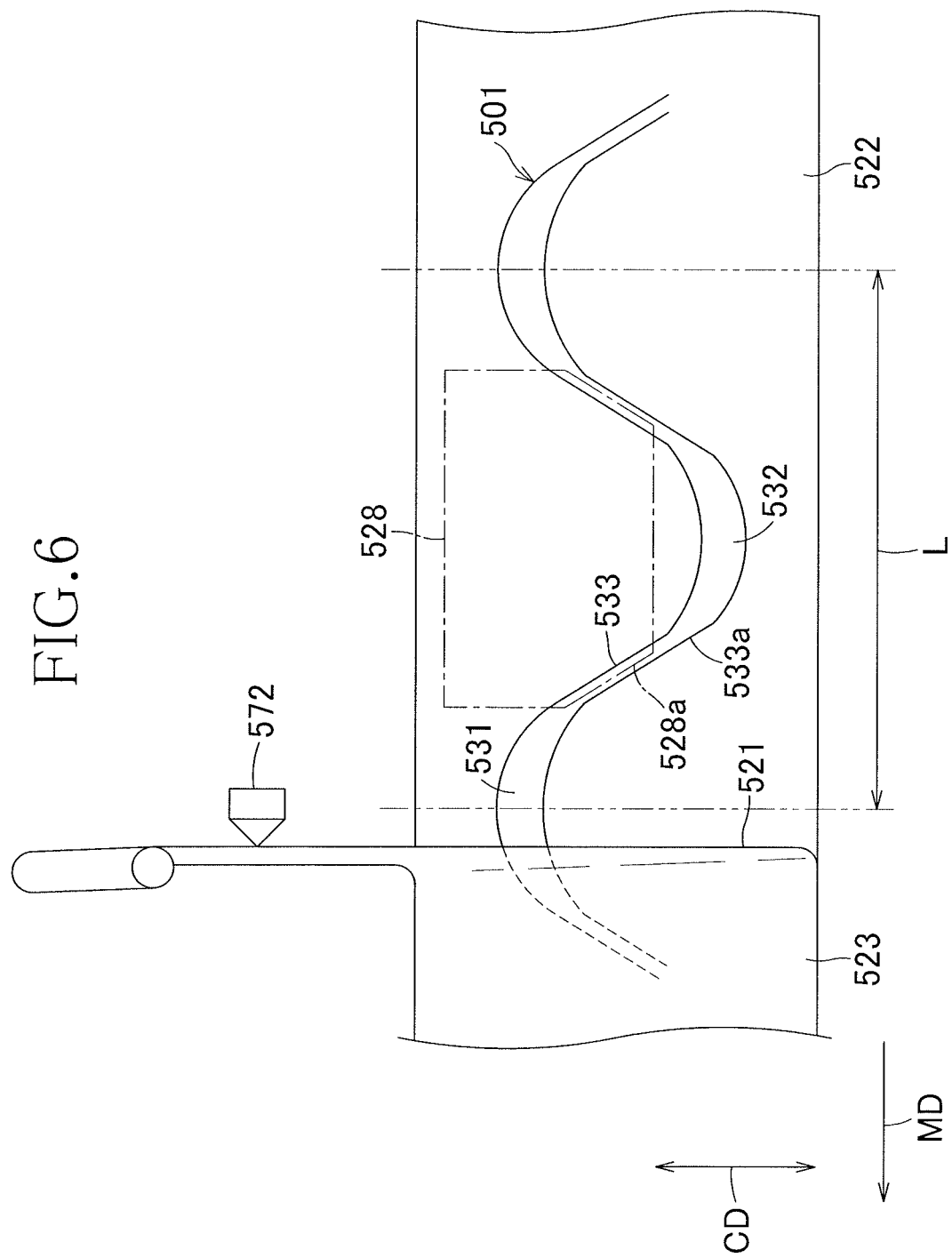
FIG. 6 is a diagram exemplarily illustrating a pattern in which elastic web is bonded to a fibrous nonwoven fabric web.

FIG. 6 is a partial plan view of the second nonwoven fabric web 522 to which the elastic web 501 has been bonded. On the left-hand in FIG. 6, the first nonwoven fabric web 521 and the composite web 523 also are shown. An imaginary line 528 on the second nonwoven fabric web 522 indicates a predetermined line along which the front sheet assembly 270 is to be cut off the composite web 523 of FIG. 6. While illustration of the front side waist-elastic member $13_F$ to be attached to the front sheet assembly 270 is eliminated from the composite web 523 in FIG. 6, the front side leg members $13_F$ or the elastic web (not shown) formed of such members $13_F$ continuously arranged in the machine direction MD may have been attached under tension in the machine direction MD to the first nonwoven fabric web 522.

According to one embodiment of the process using the steps as illustrated in FIGS. 4 and 5 to obtain the composite web 523 shown in FIG. 6, the second nonwoven fabric web 522 corresponds to the outer sheet 272 in the diaper 1. As this second nonwoven fabric web 522, spun bonded nonwoven fabrics made of polypropylene fibers and having a mass per unit area of about 25 g/m$^2$ is used and fed in the machine direction MD at a rate of about 70 m/min. As the raw fabric 500 for the elastic web 501, spun bonded nonwoven fabric, for example, of polyurethane fibers of about 47% by mass and polypropylene fiber of about 53% by mass is used. The spun bonded nonwoven fabric has a mass per unit area of about 30 g/m$^2$ and a width dimension of about 80 mm. Such raw fabric 500 is elastically stretched at a ratio of about 3.0 in the machine direction MD and fed in the form of the elastic web 501 to the guide roll 564 as illustrated in FIG. 5. This elastic web 501 has been coated with hot melt adhesives at a rate of about 3 g/m$^2$. The rocking arm 561 has its amplitude set to about 166 mm and is rocked in such a mode that the second nonwoven fabric web 522 runs by a length L of about 340 mm in the machine direction MD for each cycle of the rocking arm's movement. The elastic web 501 guided by the rocking arm 561 is fed, in a generally sine-wave pattern, onto the second nonwoven fabric web 522. Under the rocking operation of the arm 561, the elastic web 501 has its width dimension enlarged along crest segments 531 and the trough segments 532. Along intermediate segments 533 each defined between a pair of the adjacent crest segment 531 and the trough segment 532, a plurality of gathers (not shown) undulating in the transverse direction and the width dimension of the elastic web 501 us correspondingly reduced as illustrated. Depending on the operating condition of the equipment of FIGS. 4 and 5 as well as the stretch properties of the raw fabric 500, the elastic web 501 obtained by stretching the raw fabric 500 having a width dimension of about 80 mm before it is stretched has its stretch ratio and width dimension varied in the course of being fed onto the second nonwoven fabric web 522 via the rocking arm 561. Specifically, the stretch ratio along the crest segment 531 and the trough segment 532 of the curve becomes lower than the stretch ratio along the intermediate segment 533. More specifically, the width dimension of the raw fabric 500 is reduced to about 32 mm along the crest segment 531 and the trough segment 532 and to about 21 mm at the narrowest portion along the intermediate segment 533. While the elastic web 501 is formed along the intermediate segment 533 with a plurality of gathers (not shown) extending in the length direction, the crest segment 531 and the trough segment 532 are substantially free from such gathers. The first nonwoven fabric web 521 lapped on the second nonwoven fabric web 522 corresponds to the inner sheet 271 in the diaper 1. Spun bonded/melt blown/spun bonded nonwoven fabrics (SMS nonwoven fabrics) made of polypropylene fibers having a mass per unit area of about 15 g/m$^2$ and width dimension of about 200 mm used as this first nonwoven fabric web 521 has been coated with hot melt adhesives at a rate of about 3 g/m$^2$. The composite web 523 formed of these first and second nonwoven fabric webs 521, 522 and the elastic web 500 is cut out in a shape as illustrated by the imaginary line 528 in FIG. 6 and used as the front sheet assembly 270 of FIG. 2. The intermediate segments 533 of the elastic web 501 are laid on the front sheet assembly to form the belt-like front leg elastic members $14_F$.

An imaginary line 528 in FIG. 6 is a predetermined line along which the rear sheet assembly 280 (See FIGS. 2 and 3) will be cut out from the composite web 523. Assumed that the first nonwoven fabric web 521 is used as the rear sheet assembly 280, the rear sheet assembly 280 is used as one of the inner sheet 281 and the outer sheet 282 and the second nonwoven fabric web 522 is used as the other of the inner sheet 281 and the outer sheet 282. While the rear sheet assembly 280 obtained by the process as illustrated in FIG. 6 is the same as the front sheet assembly 270 so long as the shape and the component webs are concerned, it is possible to implement the present invention so that the front sheet assembly 270 and the rear sheet assembly 280 are different from each other in view of the shape or the component webs.

Figure 7:
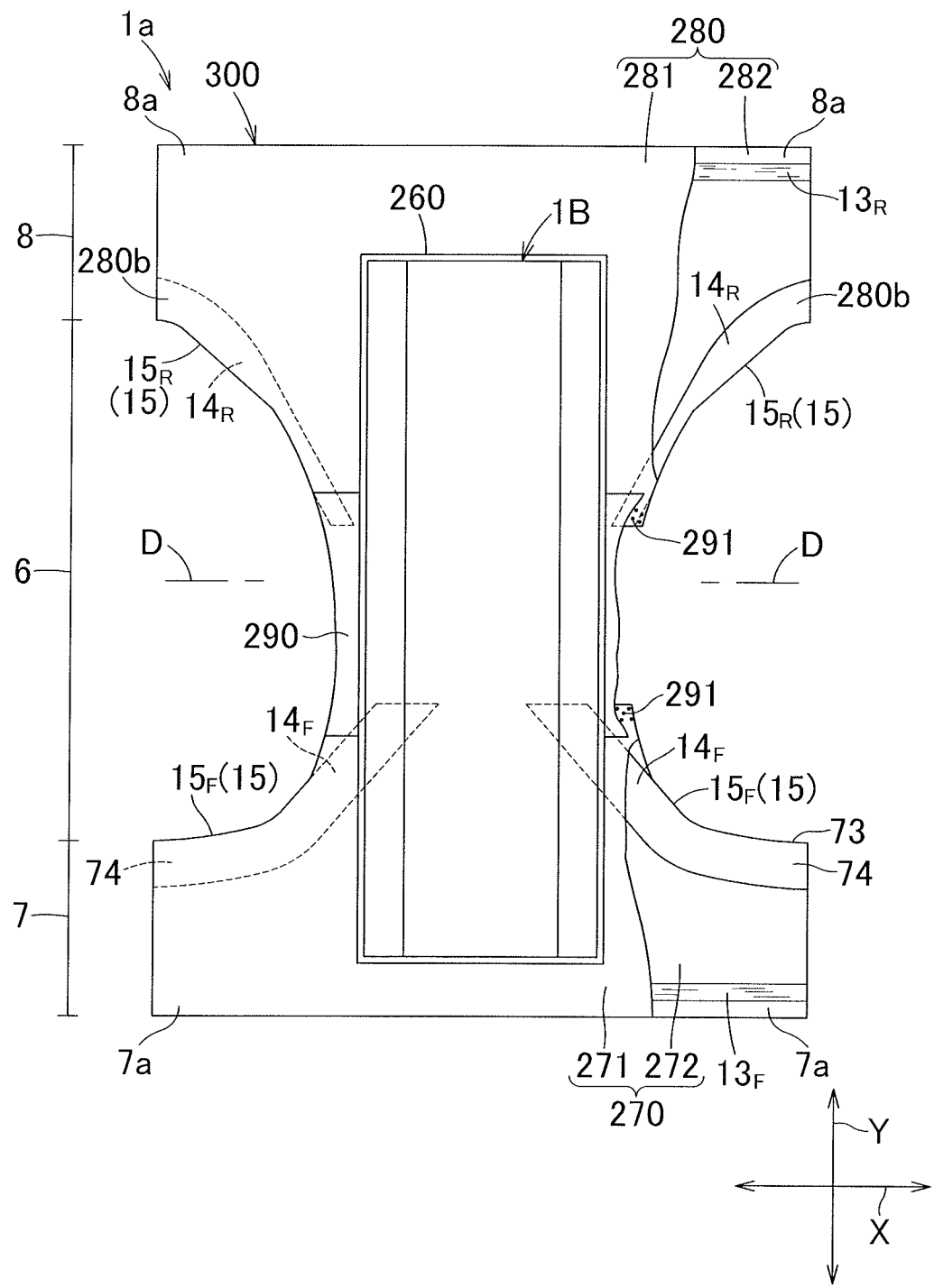
FIG. 7 is a view similar to FIG. 2, exemplarily showing one embodiment of the present invention.

FIG. 7 is a partially cutaway plan view similar to FIG. 2, showing another embodiment of the present invention. From the developed diaper la shown in FIG. 7 also, it is possible to obtain a diaper (not shown) having the same outer shape as the diaper 1 of FIG. 1. In the developed diaper la shown in FIG. 7, the regions similar to those shown in FIGS. 1 and 2 are designated by the reference numerals similar to those in FIGS. 1 and 2. It should be noted here that respective planar shapes of the front sheet assembly 270, the rear sheet assembly 280, the front side leg elastic members $14_F$ and the rear side leg elastic members $14_R$ are different from those in FIG. 2. It should be also noted that the general shapes of the belt-like front side leg elastic members $14_F$ and the belt-like rear side leg elastic members $14_R$ are indicated by solid lines and chain lines in FIG. 7. In the developed diaper la of FIG. 7, the front sheet assembly 270 and the rear sheet assembly 280 are bonded to a sheet strip 290 of nonwoven fabric with hot melt adhesives 291 to form an hourglass-shaped chassis 300. To this chassis 300, the central sheet 260 and the bodily fluid-absorbent structure 1B shown in FIG. 3 are attached. The belt-like front side leg elastic members $14_F$ included in the front sheet assembly 270 of the developed diaper 1a shown in FIG. 7 is sandwiched between the inner sheet 271 and the outer sheet 272 wherein the front side leg elastic members $14_F$ cooperate with these inner and outer sheets 271, 272 to define the front side peripheral edges $15_F$. The front side peripheral edges $15_F$ are different from those in the embodiment as shown in FIG. 2 in that they have curved shapes. The belt-like rear side leg elastic members $14_R$ included in the rear sheet assembly 280 shown in FIG. 7 are also sandwiched between the inner sheet 281 and the outer sheet 282 wherein the rear side leg elastic members $14_R$ cooperate with these inner and outer sheets 281, 282 to define the rear side peripheral edges $15_R$. The rear side peripheral edges $15_R$ also are different from those in the embodiment as shown in FIG. 2 in that they have a curved shape. Also in the diaper 1 obtained from such developed diaper la, the inner and outer sheets 271, 272 as well as the inner and outer sheets 281, 282 get finely wrinkled but, as the diaper 1 shown in FIG. 1 is the case, these sheets 271, 272, 281, 282 are not formed with frills upon contraction of the front side leg elastic members $14_F$ and the rear side leg elastic members $14_R$. The belt-like front side leg elastic members $14_F$ respectively extending and curving along the front side peripheral edges $15_F$ and the rear side leg elastic members $14_R$ respectively extending and curving along the rear side peripheral edges $15_R$ are under tension in the direction in which these elastic members $14_F$, $14_R$ extend and curve as will be apparent from FIG. 8. Consequently, this embodiment is distinguished from the first embodiment in that respective upper halves of the entire peripheral edges 15 of the leg-openings 12 can be put in close contact about the wearer's thighs at a high fit.

FIG. 8 is a diagram similar to FIG. 6, partially illustrating the step of making the rear sheet assembly 280 shown in FIG. 7. In the step illustrated in FIG. 8, the feed rate of the second nonwoven fabric web 522 shown in FIG. 4 or the operating condition mode of the rocking arm 561 such as the period and the amplitude may be adjusted to vary the sine curves of the elastic web 501 as illustrated by FIG. 6. In this way, the rear sheet assembly 280 having the size and the dimension defined by the predetermined line 528 from the composite web 523 can be obtained. To obtain the front sheet assembly 280 shown in FIG. 7 can be obtained also by appropriately adjusting the feed rate of the second nonwoven fabric web 522 or the operating condition mode of the rocking arm 561 such as the period and the amplitude. Specifically, the front side leg elastic members $14_F$ extending and curving along the front side peripheral edges $15_F$ of the entire peripheral edges 15 and the rear side leg elastic members $14_R$ extending and curving along the rear side peripheral edges $15_R$ can be obtained by appropriately adjusting the feed rate of the second nonwoven fabric web 522 or the operation mode of the rocking arm 561 such as the period and the amplitude n the equipment exemplarily illustrated in FIGS. 5 and 6.

Placement mode of the front side leg elastic members $14_F$ and the rear side leg elastic members $14_R$ relative to the diaper 1 is not limited to the exemplarily illustrated placement. For example, it is possible without departing from the scope of the present invention to apply the placement mode of the front side leg elastic members $14_F$ in the illustrated embodiment to the rear side leg elastic members $14_R$ and to apply the placement mode of the rear side leg elastic members $14_R$ in the illustrated embodiment to the front side leg elastic members $14_F$. The present invention having been described on the basis of the pants-type disposable diaper may be applicable also to the other pants-type wearing articles such as disposable pants, disposable pants for incontinent patient and toilet-training pants.

REFERENCE SIGNS LIST 1 wearing article (diaper)
6 crotch region
7 front waist region
7a side edges
8 rear waist region
8a side edges
9a (sealing) spots
12 leg-openings
$14_F$ belt-like leg elastic member
$14_R$ belt-like leg elastic member
$15_F$ peripheral edge (front side peripheral edge)
$15_R$ peripheral edge (rear side peripheral edge)
50 put flat and joined together regions
73 lower edge
83 lower edge
271 sheet-like member
281 sheet-like member
H dimension
$h_F$ dimension
$h_R$ dimension
X transverse direction
Y front-back direction
Z vertical direction

The invention claimed is:

1. A disposable pants-type wearing article having a front-back direction, a vertical direction and a transverse direction being orthogonal to one another, the article comprising:
 a front waist region and a rear waist region opposed to each other in the front-back direction and a crotch region extending between the front and rear waist regions;
 joined regions formed by putting flat and joining together the front and rear waist regions along respective side edges of the front and rear waist regions respectively opposed in the transverse direction and extending in the vertical direction;
 an absorbent structure in the crotch region;
 a waist-opening and a pair of leg-openings formed by the front and rear waist regions with the crotch region; and
 leg elastic members extending under tension along respective peripheral edges of the leg-openings,
 wherein the leg elastic members respectively have inner surfaces configured to face a wearer's skin and outer surfaces opposite to the inner surfaces, at least one of the inner and outer surfaces is bonded to a sheet member included in the joined regions and the crotch region, and
 wherein the leg elastic members include
  a pair of front side leg elastic members extending from the joined regions and along a front portion of the peripheral edges of the leg-openings, and
  a pair of rear side leg elastic members extending from the joined regions and along a rear portion the peripheral edges of the leg-openings,
 the front side leg elastic members are isolated from the rear side leg elastic members, and
 the sheet member extends along the peripheral edges of the leg-openings over ranges in which the leg elastic members extend along the peripheral edges of the leg-openings,
 wherein the peripheral edges of the leg-openings are curved lines, and the leg elastic members are in a curved state along the curved lines when the wearing article is kept flat under tension in the vertical direction as well as in the transverse direction, and
 wherein the pair of rear side leg elastic members overlaps the absorbent structure in a thickness direction, and the pair of front side leg elastic members does not overlap the absorbent structure in the thickness direction.

2. The wearing article defined by claim 1, wherein a dimension of the range in which the leg elastic members extend as measured in the vertical direction is at least 30% of a dimension of the leg-openings as measured in the vertical direction when the wearing article is kept flat under tension in the vertical direction as well as in the transverse direction.

3. The wearing article defined by claim 1, wherein the crotch region is not formed over the range in which the leg elastic members extend with frills even when the leg elastic members contract.

4. The wearing article defined by claim 1, wherein
 the front and rear leg elastic members have edges coinciding with peripheral edges of the sheet member to define the front portion and the rear portion of the peripheral edges of the leg-openings, respectively.

5. The wearing article defined by claim 1, wherein
 the front side leg elastic members are isolated from each other in the front waist region, and
 the rear side leg elastic members are isolated from each other in the rear waist region.

6. The wearing article defined by claim 1, wherein
the front waist region is defined by the sheet member, and
the rear waist regions is defined by another sheet member separated from the sheet member of the front waist region.

7. The wearing article defined by claim 6, wherein
the sheet member includes an edge opposing an edge of said another sheet member in the front-back direction, and
each of the pairs of front side leg elastic members extends from a lower edge of the joined region in the vertical direction to the edge of the sheet member.

* * * * *